United States Patent [19]

Hachmann et al.

[11] Patent Number: 5,126,242

[45] Date of Patent: Jun. 30, 1992

[54] PROCESS FOR THE STABILIZATION OF BIOLOGICALLY ACTIVE SUBSTANCES IMMOBILIZED ON SOLID PHASES

[75] Inventors: Henning Hachmann, Frankfurt am Main; Peter Molz, Mainz; Stephan Neuenhofer, Sulzbach; Gerd Schnorr, Bad Vilbel; Guido Simons, Ingelheim; Heinz-Jürgen Skrzipczyk, Bad Soden am Taunus; Kurt E. Weimer, Mörfelden, all of Fed. Rep. of Germany

[73] Assignee: Hoechst Aktiengesellschaft, Frankfurt am Main, Fed. Rep. of Germany

[21] Appl. No.: 536,809

[22] Filed: Jun. 12, 1990

[30] Foreign Application Priority Data

Jun. 14, 1989 [DE] Fed. Rep. of Germany ....... 3919393

[51] Int. Cl.$^5$ ........................................... G01N 33/535

[52] U.S. Cl. ..................................... 435/7.9; 435/188; 435/963; 436/531; 436/810; 436/534; 436/526; 530/815; 427/2; 428/407

[58] Field of Search ................ 435/7.9, 176, 180, 188, 435/963; 436/531, 548, 534, 810, 526; 530/815; 427/414, 337, 338, 222, 2; 428/403, 407

[56] References Cited

U.S. PATENT DOCUMENTS 4,652,517  3/1987  Scholl et al. ............................. 435/5

Primary Examiner—Esther L. Kepplinger
Assistant Examiner—Susan C. Wolski
Attorney, Agent, or Firm—Finnegan, Henderson, Farabow, Garrett and Dunner

[57] ABSTRACT

The invention relates to a process for the stabilization of biologically active substances which are immobilized on a carrier, where the solid phase with the immobilized biologically active substance is contacted for the stabilization with a solution which contains polyanetholesulfonic acid and/or salts thereof. The biologically active substances are, in particular, antibodies.

13 Claims, No Drawings

PROCESS FOR THE STABILIZATION OF BIOLOGICALLY ACTIVE SUBSTANCES IMMOBILIZED ON SOLID PHASES

DESCRIPTION

The present invention relates to a process for the stabilization of biologically active substances which are immobilized on a carrier (solid phase), and to carriers for carrying out immunochemical detection methods, on which the biologically active substances stabilized with the process according to the invention are immobilized.

Many immunochemical detection methods for the quantitative and qualitative determination of therapeutically and/or diagnostically important substances are based on the solid-phase principle in which a carrier (solid phase) which is insoluble in water is coated with biologically active material, i.e. the biologically active material is immobilized on the carrier. This makes it possible very easily to separate the bound from the unbound fraction of an analyte, and to separate the bound analyte from all interfering factors in the sample. Examples of suitable solid phases are synthetic or natural polymers such as polystyrene, polypropylene, PVC or latex in various geometrical embodiments, such as tubes, beads or microtiter plates.

However, the coated carriers have the disadvantage that the activity of the biologically active substances diminishes after storage times which are more or less long. These losses in activity can be compensated by increased use of coating material during manufacture only up to a certain limit. The biologically active material can be stabilized (treated) to avoid this disadvantage.

Various processes for the stabilization of the biologically active material are described, thus the use of sugars in DE-B 29 10 707, the use of sugars and proteins in EP-A 0 140 489, the use of hydrolyzed ovalbumin in EP-A 0 170 983, the use of saccharic acids and salts thereof in EP-A 0 133 976. However, the stabilities which are achieved are still not satisfactory in many respects, which becomes evident from a decrease in the capacity to bind to the analyte to be detected—expressed as the ratio of the binding of any desired standard and of the total activity—and from the reproducibility of the measurements no longer being guaranteed—expressed as the coefficient of variation CV.

The object on which the invention is based was thus to find a stabilizing material which guarantees an improved stabilization of the immobilized biologically active material and a satisfactory reproducibility of the measurements. In particular, the intention is to guarantee the reproducibility of the measurements even after prolonged or inappropriate storage of the coated solid phase.

Surprisingly, treatment with polyanetholesulfonic acid alone or together with other stabilizing materials resulted in a high stability of the immobilized biologically active material and an excellent reproducibility of the measurements.

Accordingly, the present invention relates to a process for the stabilization of biologically active substances which are immobilized on a carrier, which comprises contacting the solid phase with the immobilized biologically active substance for the stabilization with a solution which contains polyanetholesulfonic acid and/or salts thereof.

Polyanetholesulfonic acid (PASA) is a polymer of anetholesulfonic acid of the formula I

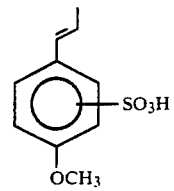

(I)

with a molecular weight of about 8,000 to 12,000. PASA with a molecular weight of 9,000 to 11,000 is recommended for the use according to the invention. Besides free polyanetholesulfonic acid, it is also possible according to the invention to employ salts thereof. Salts of polyanetholesulfonic acid which are preferably used are the alkali metal salts and, of these, in particular the sodium and/or potassium salts.

Examples of suitable carriers (solid phase) which are insoluble in water are: natural and synthetic, organic and inorganic polymers, such as polystyrene, polypropylene, polyvinyl chloride, polyvinylidene fluoride, latex, polyacrylamide, magnetite or porous glass powder. The carriers can be designed, for example, as test tube, titer plate, cuvette, rod or bead. Particularly suitable carriers for the biologically active substances are polystyrene tubes and polystyrene beads or latex beads. Where appropriate for the purpose, the carriers can also be composed of magnetic or magnetizable material or at least contain the latter, which has the advantage that these carriers can easily be removed from other systems using a magnet.

Suitable immunometric determination methods are radioimmunoassays (RIA), enzyme immunoassays (EIA) or chemiluminescence immunoassays (CIA or LIA).

The biologically active material with which the carrier is coated is, for example, an antigen, an antibody or a hapten. Preferred antibodies are those against carcinoembryonic antigen (CEA). Particularly preferred are monoclonal antibodies against CEA, which are prepared in a manner known per se.

The best procedure for the stabilization of the biologically active substance immobilized on the carrier is to contact the carrier, which has been coated with biologically active substances by known processes, with a solution which contains polyanetholesulfonic acid and/or one of the salts thereof and, where appropriate, other stabilizing agents (treatment agents) too. Other treatment agents which can be employed, besides PASA and/or salts thereof, and may be mentioned are: polymethylhydrogensiloxane, polyethylene glycol (in particular that with a molecular weight of 20,000—50,000), polyacrylic acid, polyvinylpyrrolidone, polyvinylpolypyrrolidone, polyvinyl alcohol, polypropylene glycol, lecithin, sorbitol, Tylose, sucrose, casein, gelatin, bovine serum albumin. The pH of the treatment solution should be between 5 and 9, in particular between 7 and 8. To achieve this pH, PASA and/or one or more of the salts thereof and, where appropriate, the other treatment agent or agents are dissolved in a buffer solution which is adjusted to the desired pH. Examples of suitable buffers are tris(hydroxymethyl)aminomethane, citric acid, trisodium citrate, sodium azide, hydrochloric acid or sodium hydroxide solution, or else any desired mixtures of these substances. The buffered treatment solution ready for use contains PASA and/or one or more of the salts thereof in a concentration of from 0.01 to 50 g/l (based on the treatment solution), preferably from 0.1 to 20 g/l, particularly preferably from 1 to 10 g/l. If the buffered treatment solution ready for use also contains other treatment agents, the latter are present in concentrations of from 0.1 to 40 g/l, preferably from 1 to 20 g/l, particularly preferably from 5 to 15 g/l (based on the treatment solution).

The treatment takes place by contacting the coated carrier with the treatment solution. Depending on the geometric design of the coated carriers, either the latter are completely covered by the treatment solution (for example when in the form of beads, rods etc.) or the treatment solution is placed inside the carriers (for example when in the form of tubes, cuvettes etc. which are coated from the inside). The exposure time is 5–50 hours, preferably 10–30 hours, particularly preferably 15–25 hours. The treatment is carried out at temperatures of 18°–28° C., preferably of 20°–26° C. The treatment solution is subsequently removed, and the coated, treated carriers are dried, preferably by drying in vacuo, for example at room temperature and under a pressure of 5–20 mbar for 1–5 hours. The carriers treated according to the invention can be stored at room temperature. Compared with conventionally treated carriers, for example those treated with bovine serum albumin, sucrose or sorbitol, the carriers treated according to the invention have improved stability and excellent reproducibility of the measurements.

EXAMPLES

Example 1

Preparation of the treatment buffer 6 g of tris(hydroxymethyl)aminomethane, 3.2 g of citric acid, 10 g of trisodium citrate.2H$_2$O and 1 g of sodium azide are dissolved in one liter of deionized water, and the pH is adjusted to 7.5 with HCl or NaOH.

Example 2

Preparation of the treatment solution

The desired amount of the sodium salt of polyanetholesulfonic acid Na PASA (Sigma, Sigma Chemie, Deisenhofen, or FLUKA, Feinchemikalien GmbH, Neu-Ulm) is dissolved in the treatment buffer. Solutions with the following Na PASA contents were prepared:

| Example No. | % by weight Na PASA |
|---|---|
| 2a | 0.1 |
| 2b | 0.2 |
| 2c | 0.5 |
| 2d | 1.0 |

A treatment solution which contained 0.5 % Na PASA and 0.5% bovine serum albumin (BSA) was also prepared (Example 2e).

Example 3

Polystyrene tubes (length 75 mm, diameter 12 mm) are coated on the inside to a height of about 5 mm (about 200 μl) in a conventional manner with monoclonal mouse antibodies against CEA. 300 μl of the treatment solution from Example 2a are placed in these tubes, and the latter are left to stand, covered, at room temperature for 20 hours. The treatment solution is then removed by aspiration, and the tubes are dried at room temperature under a pressure of 10 mbar for 3 hours.

Example 4

Coated polystyrene tubes are treated in analogy to Example 3 with the treatment solution from Example 2b.

Example 5

Coated polystyrene tubes are treated in analogy to Example 3 with the treatment solution from Example 2c.

Example 6

Coated polystyrene tubes are treated in analogy to Example 3 with the treatment solution from Example 2d.

Example 7

Coated polystyrene tubes are treated in analogy to Example 3 with the treatment solution from Example 2e.

Determination of the stability and the reproducibility

The treated tubes from Examples 3 to 7 were subjected to a heat stress. For this, they were each stored in a cold room (4° C., 60% humidity) for 6 days, then in a tropical room (40° C., 80% humidity) for 6 days and thereafter in an air-conditioned room (alternating: 40° C., 80% humidity for 12 h; 5° C., 60% humidity for 12 h) for a further 6 days. Subsequently the binding values ($S_6$/T in %) and coefficient of variation (CV in %) were measured for all the treated tubes from Examples 3 to 7. The binding value $S_6$/T results from the ratio of: signal of the bound tracer when the highest standard ($S_6$ of the RIA-gnost CEA) is used and signal of the amount of tracer (total activity T) employed per tube, and the coefficient of variation CV (in %) is calculated from the standard deviation of 10 measurements (SD) and the average of these 10 measurements (mean) as (SD/mean)·100. The results obtained are shown in Table 1 (stress: air-conditioned room, and tropical room where appropriate). Table 1 contains a tube treated with 1% BSA as comparison example.

The tubes treated according to the invention have, by comparison with the conventionally treated tubes, a better stability and thus a better reproducibility of the measurements.

TABLE 1

| | | Storage in | | $S_6/T$ after stress (10 determinations) | |
|---|---|---|---|---|---|
| Treated with | Initial binding ($S_6/T$) | Air-conditioned room | Tropical room | % binding ($S_6/T$) | CV % |
| 1.0% BSA (comp. Ex.) | 52% | 19 d | | 15 | 16.9 |
| 0.1% Na PASA (Ex. 3) | 46% | 19 d | | 46 | 2.1 |
| 0.2% Na PASA (Ex. 4) | 46% | 19 d | | 45 | 1.7 |
| 0.5% Na PASA (Ex. 5) | 47% | 19 d | | 45 | 2.3 |
| 1.0% Na PASA (Ex. 6) | 47% | 19 d | | 41 | 1.7 |
| 1.0% BSA (comp. Ex.) | 47% | 6 d | 6 d | 22 | 11.0 |
| 1.0% Na PASA (Ex. 6) | 38% | 6 d | 6 d | 42 | 2.0 |

We claim:

1. A process for stabilizing a biologically active substance immobilized on a solid phase, comprising contacting said solid phase immobilized biologically active substance with a stabilizing solution comprising polyanethelesulfonic acid and/or salts thereof in a concentration between 0.01 and 50 g/l.

2. The process as claimed in claim 1, wherein the solution also contains other stabilizing agents.

3. The process as claimed in claim 1, wherein the solution contains a buffer.

4. The process as claimed in claim 1, wherein the solid phase is subsequently dried.

5. The process as claimed in claim 1, wherein the biologically active substance is an antibody.

6. The process as claimed in claim 1, wherein the biologically active substance is a monoclonal antibody.

7. The process as claimed in claim 1, wherein the biologically active substance is an antigen.

8. The process as claimed in claim 1, wherein the solid phase is composed of latex particles or is a polystyrene tube.

9. The process as claimed in claim 1, wherein the solid phase can be magnetically attracted.

10. The process as claimed in claim 1, wherein the solid phase is a synthetic polymer 11. A process for preparing a stabilized immunoreactive solid phase for carrying out an immunochemical detection, comprising (i) immobilizing a biologically active substance to form an immunoreactive solid phase and (ii) contacting the immunoreactive solid phase with a stabilizing solution comprising polyanetholesulfonic acid and/or salts thereof in a concentration between 0.01 and 50 g/l.

12. A stabilized immunoreactive solid phase for carrying out an immunochemical detection prepared by the method as claimed in claim 11.

13. In a method for performing a radioimmunoassay, enzyme immunoassay, or chemiluminescence immunoassay to detect an analyte in a sample, comprising contacting said sample with an immunoreactive solid phase comprising immobilized analyte or specific binding partner thereof and detecting the amount of bound or free sample analyte, wherein the improvement comprises stabilizing the immunoreactant solid phase by contacting said solid phase with a stabilizing solution comprising polyanetholesulfonic acid and/or salts thereof in a concentration between 0.01 and 50 g/l prior to contacting said sample.

* * * * *